(12) United States Patent
Gasparyan et al.

(10) Patent No.: US 12,616,805 B2
(45) Date of Patent: May 5, 2026

(54) NON-COMBUSTIBLE AEROSOL DELIVERY SYSTEM, FILTER UNIT AND ASSEMBLY

(71) Applicant: Nicoventures Trading Limited, London (GB)

(72) Inventors: Hripsime Gasparyan, London (GB); Simon James Copley, St. Ives (GB); Daniel Thomas Ahearn, St. Ives (GB); Francesca Alys Stephens, St. Ives (GB)

(73) Assignee: Nicoventures Trading Limited, London (GB)

( * ) Notice: Subject to any disclaimer, the term of this patent is extended or adjusted under 35 U.S.C. 154(b) by 604 days.

(21) Appl. No.: 18/002,106

(22) PCT Filed: Jun. 16, 2021

(86) PCT No.: PCT/GB2021/051532
§ 371 (c)(1),
(2) Date: Dec. 16, 2022

(87) PCT Pub. No.: WO2021/255455
PCT Pub. Date: Dec. 23, 2021

(65) Prior Publication Data
US 2023/0241333 A1 Aug. 3, 2023

(30) Foreign Application Priority Data
Jun. 17, 2020 (GB) ..................................... 2009252

(51) Int. Cl.
*A61M 15/06* (2006.01)
*A61M 11/04* (2006.01)

(52) U.S. Cl.
CPC .......... *A61M 15/06* (2013.01); *A61M 11/041* (2013.01); *A61M 2205/8206* (2013.01)

(58) Field of Classification Search
None
See application file for complete search history.

(56) References Cited

U.S. PATENT DOCUMENTS

| 9,402,422 B2 | 8/2016 | Shenkal |
| 10,470,498 B2 | 11/2019 | Shenkal et al. |
| | (Continued) | |

FOREIGN PATENT DOCUMENTS

| EP | 3721726 A1 | 10/2020 |
| WO | 94/23600 A1 | 10/1994 |
| | (Continued) | |

OTHER PUBLICATIONS

"International Preliminary Report on Patentability received for PCT Patent Application No. PCT/GB2021/051532, mailed on Dec. 29, 2022", 13 pages.

(Continued)

*Primary Examiner* — Cynthia Szewczyk
(74) *Attorney, Agent, or Firm* — MERCHANT & GOULD P.C.

(57) ABSTRACT

There is provided a non-combustible aerosol delivery system for filtering exhaled breath, the aerosol delivery system including a power source; a mouthpiece; a removable filter unit; wherein in a first configuration, the filter unit is present and is in engagement with the non-combustible aerosol delivery system to provide an inhalate airflow path, adapted to convey vapor generated by the non-combustible aerosol delivery system to the user during an inhalation, and an exhalate airflow path, adapted to convey breath from the user during an exhalation into the non-combustible aerosol delivery system to the filter unit; wherein in a second configuration, the filter unit is not in engagement with the non-combustible aerosol delivery system.

17 Claims, 10 Drawing Sheets

(56)                    References Cited

U.S. PATENT DOCUMENTS

| | | | |
|---|---|---|---|
| 10,588,344 | B2 | 3/2020 | Shenkal et al. |
| 10,617,148 | B2 | 4/2020 | Shenkal et al. |
| 2019/0247606 | A1 | 8/2019 | Williams |
| 2020/0170295 | A1 | 6/2020 | Grimm et al. |
| 2020/0305505 | A1 | 10/2020 | Shenkal et al. |
| 2021/0127736 | A1 | 5/2021 | Grimm |
| 2021/0145063 | A1* | 5/2021 | Perrins ...................... A24F 7/00 |

FOREIGN PATENT DOCUMENTS

| | | | |
|---|---|---|---|
| WO | 9423599 | A1 | 10/1994 |
| WO | 2015/184250 | A1 | 12/2015 |
| WO | 2019/191840 | A1 | 10/2019 |
| WO | 2020123286 | A1 | 6/2020 |
| WO | 2020154701 | A1 | 7/2020 |
| WO | 2021092086 | A1 | 5/2021 |

OTHER PUBLICATIONS

"International Search Report and Written Opinion received for PCT Patent Application No. PCT/GB2021/051532, mailed on Nov. 29, 2021", 20 pages.
"Invitation to Pay Additional Fees received for PCT Patent Application No. PCT/GB2021/051532, mailed on Oct. 6, 2021", 11 pages.
Mexican Application No. MX/a/2022/014417, Mexican Office Action mailed Jun. 23, 2025, 7 pages.

* cited by examiner

NON-COMBUSTIBLE AEROSOL DELIVERY SYSTEM, FILTER UNIT AND ASSEMBLY

CROSS-REFERENCE TO RELATED APPLICATIONS

The present application is a National Phase entry of PCT Application No. PCT/GB2021/051532, filed Jun. 16, 2021, which claims priority from Great Britain Application No. 2009252.4, filed Jun. 17, 2020, each of which is hereby fully incorporated herein by reference.

TECHNICAL FIELD

The present disclosure relates to a non-combustible aerosol delivery system, a filter unit for engagement with a non-combustible aerosol delivery system and an assembly comprising a filter unit and a unit containing a vapor forming material.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Non-combustible aerosol delivery system including systems such as electronic cigarettes (e-cigarettes) are known. Some such systems contain a reservoir of a source liquid containing a formulation, typically including an active material such as nicotine, from which an aerosol is generated, e.g. through vaporization. An aerosol source for an aerosol delivery device may thus comprise an aerosol generating component such as a heater having a heating element arranged to receive source liquid from the reservoir, for example through wicking/capillary action. Other source materials may be similarly heated to create an aerosol, such as botanical matter, or a gel comprising an active ingredient and/or flavoring. Hence more generally, the e-cigarette may be thought of as comprising or receiving a payload for heat vaporization. Other systems may provide aerosols from substances which may comprise one or more active constituents, one or more flavors, one or more aerosol-former materials, and/or one or more other functional materials.

While, or before, a user inhales on the device, electrical power is supplied to the heating element to vaporize a portion of aerosolizable material in the vicinity of the heating element, to generate an aerosol for inhalation by the user. Such devices are usually provided with one or more air inlet holes located away from a mouthpiece end of the system. When a user sucks on a mouthpiece connected to the mouthpiece end of the system, air is drawn in through the inlet holes and past the aerosol generating component. There is a flow path connecting between the aerosol generating component and an opening in the mouthpiece so that air drawn past the aerosol source continues along the flow path to the mouthpiece opening, carrying some of the aerosol generated by the aerosol generating component with it. The aerosol-carrying air exits the aerosol delivery device through the mouthpiece opening for inhalation by the user.

In conventional systems the smoking process concludes with this aerosol-delivery stage. As of 2019 there was an estimated 3.6 million e-cigarette users in Great Britain alone (7.1% of the population).

SUMMARY

Improvements to this smoking process are disclosed herein.

In a first aspect of the disclosure there is provided a non-combustible aerosol delivery system for filtering exhaled breath, the aerosol delivery system comprising: a power source; a mouthpiece; a removable filter unit; wherein in a first configuration, the filter unit is present and is in engagement with the non-combustible aerosol delivery system to provide an inhalate airflow path, adapted to convey vapor generated by the non-combustible aerosol delivery system to the user during an inhalation, and an exhalate airflow path, adapted to convey breath from the user during an exhalation into the non-combustible aerosol delivery system to the filter unit; wherein in a second configuration, the filter unit is not in engagement with the non-combustible aerosol delivery system.

In a second aspect of the disclosure there is provided a mouthpiece for use in a non-combustible aerosol delivery system for filtering exhaled breath, wherein, in use, in a first configuration, the mouthpiece is in fluid communication with a filter of the non-combustible aerosol delivery system to provide an inhalate airflow path, adapted to convey vapor generated by the non-combustible aerosol delivery system through the mouthpiece to the user during an inhalation, and an exhalate airflow path, adapted to convey breath from the user during an exhalation through the mouthpiece to the filter unit; wherein, in use, in a second configuration, the mouthpiece is not in fluid communication with a filter of the non-combustible aerosol delivery system.

The presently disclosed system enables a user to inhale an aerosol from the aerosol delivery system and then exhale through the system. In the present disclosure, the system may process the exhalate in the filter unit by filtering it. The system also allows for provision of an aerosol to a user without use of the filter unit.

In this way, a user is able to use the system to inhale aerosol in locations where exhalation into the environment of an aerosol is undesirable which may be a variety of reasons. When in such environments or locations, the user engages the filter unit in the system and may exhale into the system, the exhalate being processed by the filter unit. Alternatively, when the user is in a location where exhalation into the environment of an aerosol is not undesirable, the user need not engage the filter unit and may use the system in a more conventional manner. In such a way, the presently disclosed system provides for flexible use of the system in different locations/environment.

When in an environment where exhalation of aerosol is undesirable, during exhalation, the user can exhale into the system rather than into the environment. Such a system can therefore operate as a personal exhalate air filter.

The present system may advantageously provide a filter unit which may be removable from the system and replaced according to usage patterns of the user. When the filter unit is depleted it may easily be replaced with another filter unit. In this way, the user may discard the consumable filter rather than say the system as a whole which saves resources of the system and is therefore cheaper for the user over the lifetime of the system.

In an example, in the first configuration the filter unit is disposed between the mouthpiece and the power source of the non-combustible aerosol delivery system. This may advantageously allow easy removal of the filter unit from the body of the system. Furthermore, this may allow for a number of more discrete designs. Furthermore, this arrangement results in the travel path for the exhalate to be shorter than if the filter was deeper into the system. In this way, the exhalate need not travel deep into the system (which might lead to condensation of the exhalate onto system components) but rather is filtered shortly after entering the system.

In an example, the system further comprises a unit containing a vapor forming material. The unit may be more easily removed from and returned to the system than vapor forming material alone. The user interacts with the unit rather than the vapor forming material which is a simpler and cleaner process. In turn, this therefore improves the user's experience of the system.

In a second aspect of the disclosure there is provided a non-combustible aerosol delivery system for filtering exhaled breath, the non-combustible aerosol delivery system comprising: a power source; a mouthpiece; a filter unit; a unit containing a vapor forming material; an inhalate airflow path, adapted to convey vapor generated by the non-combustible aerosol delivery system to the user during an inhalation, and an exhalate airflow path, adapted to convey breath from the user during an exhalation into the non-combustible aerosol delivery system to the filter unit; wherein the filter unit and the unit containing the vapor forming material together form a single assembly which is removable from the non-combustible aerosol delivery system.

Such an arrangement, as with the first aspect, enables a user to inhale an aerosol from the aerosol delivery system and then exhale through the system. In the present disclosure, the system may process the exhalate in the filter unit by filtering it. The system also allows for provision of an aerosol to a user without use of the filter unit. In this way, a user is able to use the system to inhale aerosol in locations where exhalation into the environment of an aerosol is undesirable which may be a variety of reasons.

Additionally, in such an arrangement using a single assembly, the manufacturer may be able to control the amount of vapor forming material provided per filter unit and the filter (or element which provides the filtering function of the filter unit) in the filter unit such that the amount of vapor forming material would be sufficient to provide an amount of vapor that would, under most usage patterns, be sufficient to saturate or otherwise use up the filter. In such a way, the lifetime of the vapor forming material and the filter may be matched or balanced so that, when the vapor forming material is used up, so too is the filter, the single assembly can be removed and replaced with a new single assembly. This improves the ease of use of the device and therefore improves the user's experience of the system.

In an example, the vapor forming material comprises a plant material. Plant materials may provide aerosols for inhalation within reasonable constraints and therefore may be used in such a system. In an example, the vapor forming material is a liquid.

In an example, herein the inhalate airflow path and the exhalate airflow path are entirely distinct from each other. In this way, the system prevents any exhalate being re-inhaled on a subsequent puff. Each inhalation is a new inhalation and does therefore not suffer from inclusion of unintended material. By this it is meant that re-inhalation of condensed components from the exhalate is prevented. This, in turn, allows greater control for the system over the components inhaled by a user. In turn, this improves the user's experience of the system.

In an example, the mouthpiece forms both a portion of the inhalate airflow path and a portion of the exhalate airflow path, and is configured to move between an inhalation position and an exhalation position, wherein in the inhalation position the mouthpiece is in fluid communication with the remainder of the inhalate airflow path and is not in fluid communication with the remainder of the exhalate airflow path, and wherein in the exhalation position the mouthpiece is not in fluid communication with the remainder of the inhalate airflow path and is in fluid communication with the remainder of the exhalate airflow path. By re-using a portion of the system for both the inhalate airflow path and the exhalate airflow path, advantageously this enables the system to be more compact and therefore the system can be provided in a greater number of ergonomic conformations. This, in turn, may improve the user's experience of the system.

In an example, the mouthpiece is hinged so as to rotate between the inhalation position and the exhalation position. Use of a hinge may allow the mouthpiece to rotate under either manual or automatic stimulus. A hinge is an option for providing movement in a system with a portion of the inhalate and exhalate airflow path being the same. Use of a hinge enables the system to use space which may otherwise not be used for components of the system. In this way, the hinge may allow the system to be designed in a greater number of ways, which in turn may allow for more compact designs. This may allow for a greater number of ergonomic conformations. This, in turn, may improve the user's experience of the system.

In an example, the mouthpiece is rotatable to move between the inhalation position and the exhalation position. Rotation of the mouthpiece may occur under either manual or automatic stimulus. A rotating mouthpiece is an option for providing movement in a system with a portion of the inhalate and exhalate airflow path being the same. Use of a rotating mouthpiece enables the system to use space which may otherwise not be used for components of the system. In this way, the rotating mouthpiece may allow the system to be designed in a greater number of ways, which in turn may allow for more compact designs. This may allow for a greater number of ergonomic conformations. This, in turn, may improve the user's experience of the system.

In an example, the mouthpiece has an inlet port which, in the inhalation position, is in fluid communication with the remainder of the inhalate airflow path and is not in fluid communication with the remainder of the exhalate airflow path, and an outlet port which, in the exhalation position, is not in fluid communication with the remainder of the inhalate airflow path and is in fluid communication with the remainder of the exhalate airflow path. This arrangement of an inlet port in an inhalation position and an outlet port in an exhalation position is an option for providing separation between the inhalate airflow path and the exhalate airflow path. This arrangement prevents any exhalate being re-inhaled on a subsequent puff due to the separation of the two airflow paths. Each inhalation is a new inhalation and does therefore not suffer from inclusion of unintended material. In turn, this improves the user's experience of the system.

In an example, the inlet port and the outlet port are the same. Re-using an element in the system is an option for reducing the number of components in the system. In this way, there may be fewer components which may malfunction and, in turn, the system may have a longer lifetime.

In an example, the inlet port and the outlet port are distinct from each other. Ensuring the full inhalate airflow path is separate from the exhalate airflow path allows prevention of condensation of exhalate onto any portion of the inhalate airflow path. In this way, re-inhalation of condensed components from the exhalate is prevented. This in turn allows greater control for the system over the components inhaled by a user.

In an example, the non-combustible aerosol delivery system further comprises a diverter assembly, wherein the diverter assembly comprises a multi-flap valve, wherein the flaps of the multi-flap valve have a thickness of no greater than 0.7 mm. In an example, the flaps of the multi-flap valve have a thickness of no greater than 0.5 mm. In an example, the flaps of the multi-flap valve have a thickness of no greater than 0.3 mm. In another example, the flaps of the multi-flap valve have a thickness of no greater than 0.1 mm. A multi-flap valve may be a system which has at least two flaps, one for moving to enable movement of air for inhalation and blocking exhalation and one for moving to enable movement of air for exhalation and blocking inhalation.

In an example, the filter unit contains at least one filter. The filter unit be arranged to remove aerosol droplets from the vapor. In particular, a filter may be used which comprises glass fiber, polypropylene and combinations thereof which is effective at capturing exhalate. A balance is to be struck between the filtering (exhalate capture) provided by the filter used in the system and the pressure drop during exhalation experienced by a user. Proposed embodiments herein provide a balanced system for capturing exhalate while simultaneously providing a smooth inhale and exhale action for a user. As droplets, material or particles contact filter fibers they are collected and do not re-enter the vapor and are therefore effective filters.

In an example, the filter unit further comprises a separator for separating aerosol droplets from vapor. The separator is a preferred component for removal of aerosol droplets from a vapor as the removal is reasonable while the impact on pressure during exhalation for the user is also reasonable.

In an example, the filter unit comprises at least one deodorizing filter. Advantageously, the deodorizing filter allows for removal of undesirable odor from exhaled vapor. This can therefore improve the user's experience of the system.

In an example, the non-combustible aerosol provision system is an electronic cigarette. In an example, the non-combustible aerosol provision system is an aerosol generating material heating system.

In an example, the non-combustible aerosol provision system generates aerosol using a combination of aerosol-generating materials, one or a plurality of which may be heated. Use of a plurality of aerosol-generating materials enables the system to provide a flexible and measured aerosol to the user. Greater control over the options available allows a user to control the aerosol produced to that of a bespoke aerosol tailored to the user's preferences. In this way, the user experience of the system is improved.

In a third aspect of the disclosure there is provided a filter unit configured for engagement with a non-combustible aerosol delivery system for filtering exhaled breath, wherein the aerosol delivery system comprises: a power source; a mouthpiece; wherein in a first configuration, the filter unit is in engagement with the non-combustible aerosol delivery system to provide an inhalate airflow path, adapted to convey vapor generated by the non-combustible aerosol delivery system to the user during an inhalation, and an exhalate airflow path, adapted to convey breath from the user during an exhalation into the non-combustible aerosol delivery system to the filter unit; wherein in a second configuration, the filter unit is not in engagement with the non-combustible aerosol delivery system.

6

In an example, the non-combustible aerosol delivery system is as defined in any one of examples above.

In a fourth aspect of the disclosure there is provided an assembly comprising a filter unit and a unit containing a vapor forming material, wherein the assembly is configured for engagement as a single assembly with a non-combustible aerosol delivery system for filtering exhaled breath, wherein the non-combustible aerosol delivery system comprises: a power source; a mouthpiece; an inhalate airflow path, adapted to convey vapor generated by the non-combustible aerosol delivery system to the user during an inhalation, and an exhalate airflow path, adapted to convey breath from the user during an exhalation into the non-combustible aerosol delivery system to the filter unit.

In an example, the non-combustible aerosol delivery system is as defined in any one of examples above.

Further aspects are provided in accordance with the claims.

It is to be understood that both the foregoing general summary of the disclosure and the following detailed description are exemplary, but are not restrictive, of the disclosure.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

Figure 1A:
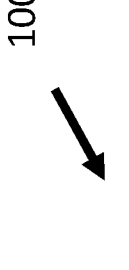
FIGS. 1A and 1B schematically show longitudinal cross-sectional views of an example of a non-combustible aerosol delivery system.

A non-combustible aerosol delivery system and filter unit are disclosed. In the following description, a number of specific details are presented in order to provide a thorough understanding of the embodiments of the present disclosure. It will be apparent, however, to a person skilled in the art that these specific details need not be employed to practice embodiments of the present disclosure. Conversely, specific details known to the person skilled in the art are omitted for the purposes of clarity where appropriate.

As described above, the present disclosure relates to a non-combustible aerosol delivery which may include an electronic aerosol delivery system or a vapor delivery device such as an e-cigarette or nebulizer. Throughout the following description the term "e-cigarette" is sometimes used but this term may be used interchangeably with (electronic) aerosol/vapor delivery system. Similarly the terms 'vapor' and 'aerosol' are referred to equivalently herein.

Generally, the non-combustible aerosol delivery device may be an electronic cigarette, also known as a vaping device or electronic nicotine delivery system, although it is noted that the presence of nicotine in the aerosolizable material is not a requirement. In some embodiments, a non-combustible aerosol delivery device is a tobacco heating system, also known as a heat-not-burn system. In some embodiments, the non-aerosolizable aerosol delivery device is a hybrid system to generate aerosol using a combination of materials, one or a plurality of which may be heated. Each of the aerosolizable materials may be, for example, in the form of a solid, liquid or gel and may or may not contain nicotine. In some embodiments, the hybrid system comprises a liquid or gel aerosolizable material and a solid aerosolizable material. The solid aerosolizable material may comprise, for example, a tobacco or a non-tobacco product. Meanwhile in some embodiments, the non-combustible aerosol delivery device generates a vapor or aerosol from one or more such aerosolizable materials.

Typically, the aerosol delivery system may comprise a non-combustible aerosol delivery device and an article for use with the non-combustible aerosol delivery device. However, it is envisaged that articles which themselves comprise a means for powering an aerosol generating component may themselves form the non-combustible aerosol delivery device.

In some embodiments, the aerosolizable material may comprise an active material, an aerosol forming material and optionally one or more functional materials. The active material may comprise nicotine (optionally contained in tobacco or a tobacco derivative) or one or more other non-olfactory physiologically active materials. A non-olfactory physiologically active material is a material which is included in the aerosolizable material in order to achieve a physiological response other than olfactory perception. The aerosol forming material may comprise one or more of glycerol, propylene glycol, diethylene glycol, triethylene glycol, tetraethylene glycol, 1,3-butylene glycol, erythritol, meso-Erythritol, ethyl vanillate, ethyl laurate, a diethyl suberate, triethyl citrate, triacetin, a diacetin mixture, benzyl benzoate, benzyl phenyl acetate, tributyrin, lauryl acetate, lauric acid, myristic acid, and propylene carbonate. The one or more functional materials may comprise one or more of flavors, carriers, pH regulators, stabilizers, and/or antioxidants.

Referring now to the drawings, wherein like reference numerals designate identical or corresponding parts throughout the several views, FIG. 1A is a schematic diagram of non-combustible aerosol delivery system 100. The non-combustible aerosol delivery system 100 is arranged for filtering exhaled breath. The non-combustible aerosol delivery system 100 has a power source 110, a mouthpiece 120 and a removable filter unit 130. In a first configuration, the filter unit 130 is present and is in engagement with the non-combustible aerosol delivery system 100 to provide an inhalate airflow path A, adapted to convey vapor generated by the non-combustible aerosol delivery system 100 to the user during an inhalation, and an exhalate airflow path B, adapted to convey breath from the user during an exhalation into the non-combustible aerosol delivery system 100 to the filter unit 130.

Figure 1A:
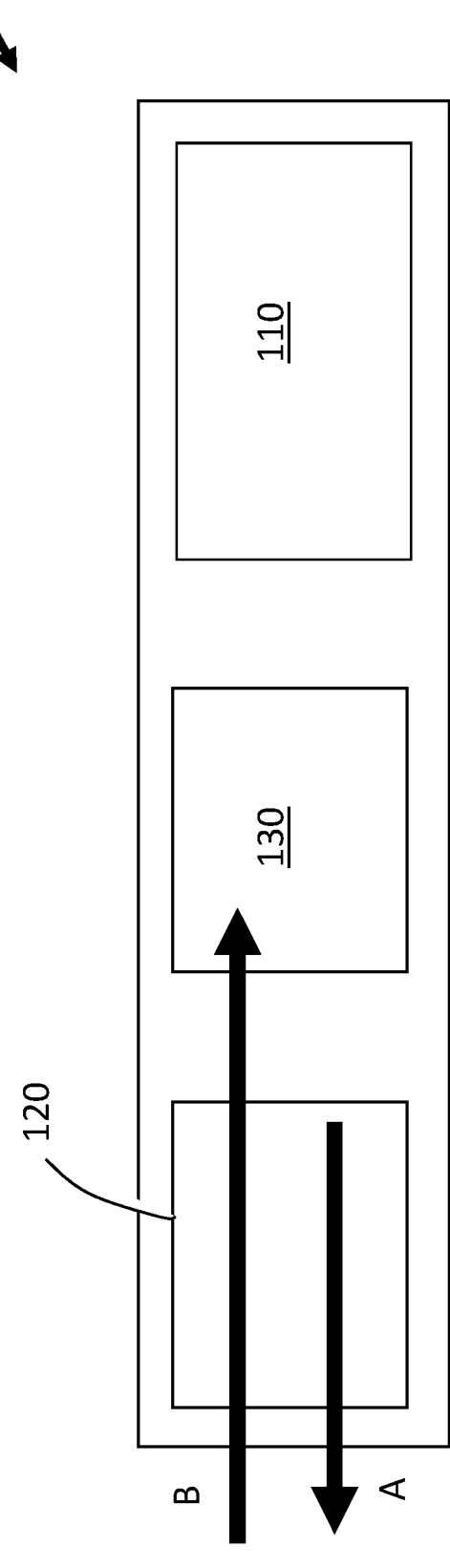
Figure 1B:
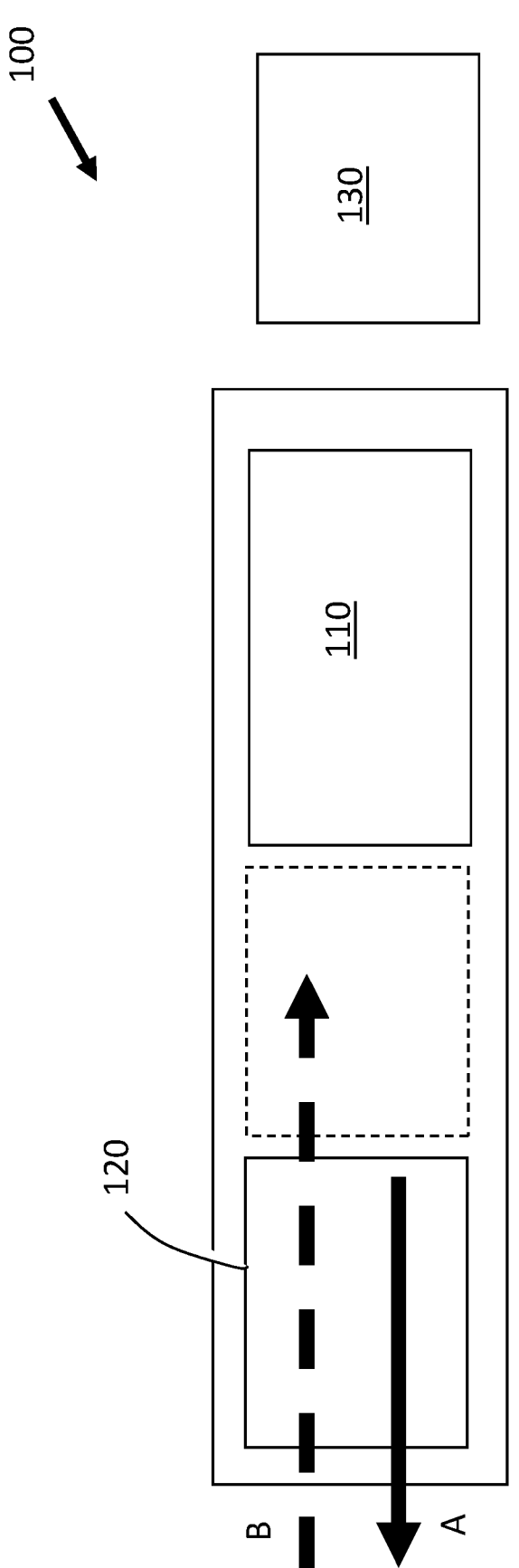

In a second configuration, shown in FIG. 1B, the filter unit 130 is not in engagement with the non-combustible aerosol delivery system 100. The filter unit 130 is shown to the side having been removed from the non-combustible aerosol delivery system 100. The position in the system 100 where the filter unit 130 would be if in engagement with the system 100 is shown in dashed line. The exhalate airflow path B is shown in dashed line accordingly as the exhalate airflow path to the filter unit 130 is no longer present. The inhalate airflow path A need not pass through the filter unit 130 and so is shown in full lines, as the system 100 may produce an aerosol for inhalation without the filter unit 130 in engagement with the system 100.

Therefore, the non-combustible aerosol delivery system 100 has an inhalate airflow path A adapted to convey vapor generated by the aerosol delivery system 100 to the user during an inhalation. The non-combustible aerosol delivery system 100 has an exhalate airflow path B, adapted to convey breath from the user during an exhalation into the non-combustible aerosol delivery system 100 to the filter unit 130. In the schematic example of FIGS. 1A and 1B, A and B are shown as passing in opposite directions through the mouthpiece 120.

The system 100 is arranged to pass breath from the user through the filter unit 130. The filter unit 130 is arranged to collect the vapor passing through the system 100 in the breath exhaled by a user. In this way, the user may optionally exhale through the system 100 when desiring to not exhale vapor. This may be particularly advantageous in areas of close proximity to others or in areas where vapor production is not allowed or discouraged. The user therefore is able to use the system 100 as a way to capture exhalate and not produce a visible exhalation.

When in an area where vapor production is not discouraged, the user may opt to remove or not engage the filter unit 130 with the system 100. In this way, the system 100 may provide an aerosol to the user and the user may exhale into the local environment.

Figure 2:
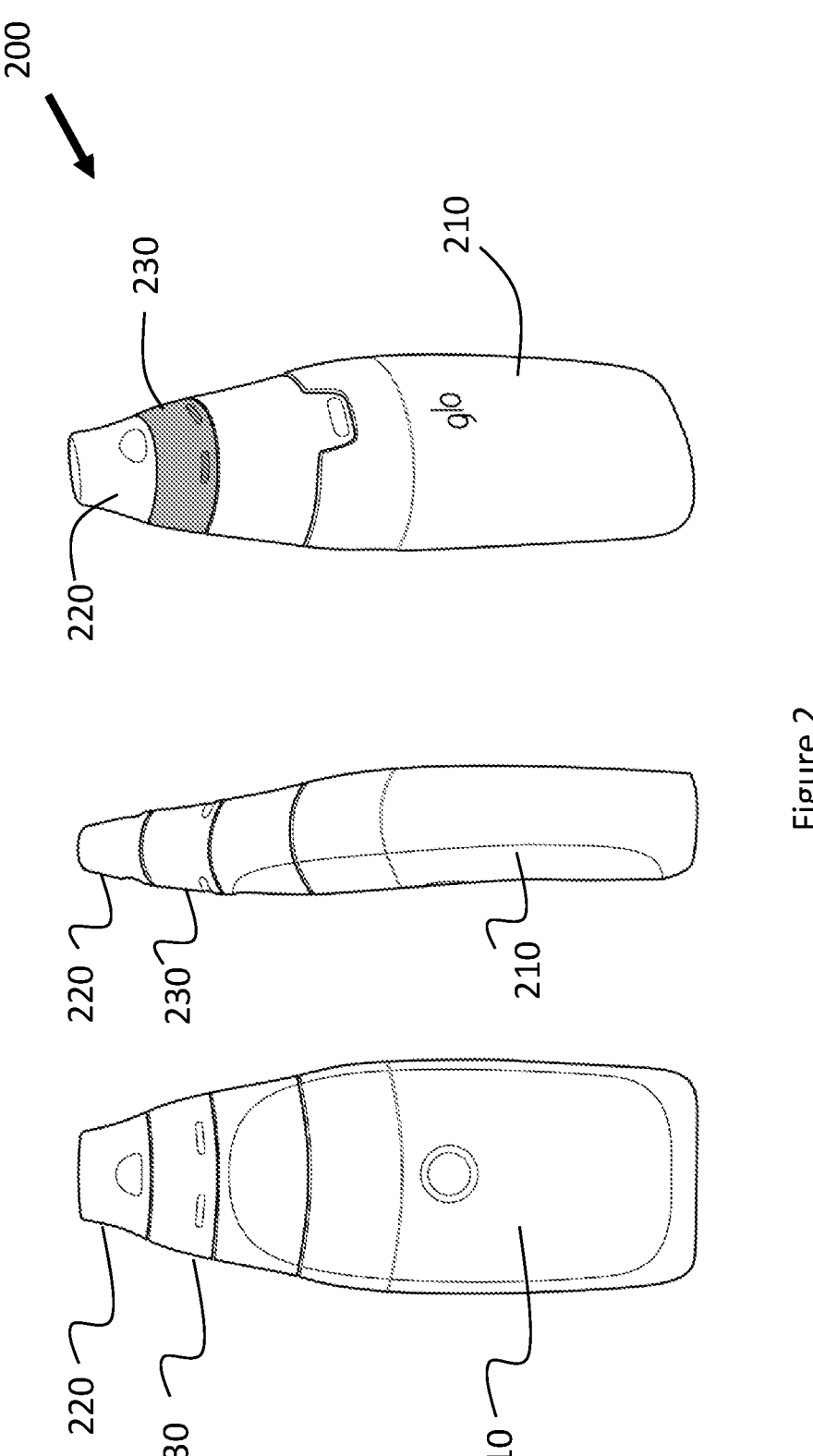
FIG. 2 schematically shows views of an example of a non-combustible aerosol delivery system.

Referring now to FIG. 2, there is shown some schematic diagrams of a non-combustible aerosol delivery system 200. The non-combustible aerosol delivery system 200 of FIG. 2 has a power source 210, a mouthpiece 220 and a filter unit 230. The system 200 in FIG. 2 is shown in the first configuration, i.e. the filter unit 230 is present and in engagement with the system 200. In the example shown, filter unit 230 is disposed between the mouthpiece 220 and the body of the system 200 which contains the power source 210 of the system 210. The system 200 is shown in front-on, side-on and perspective views in FIG. 2.

Figure 3:
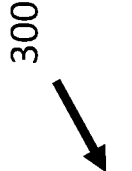
FIG. 3 schematically shows a longitudinal cross-sectional view of an example of a non-combustible aerosol delivery system.
Figure 3:
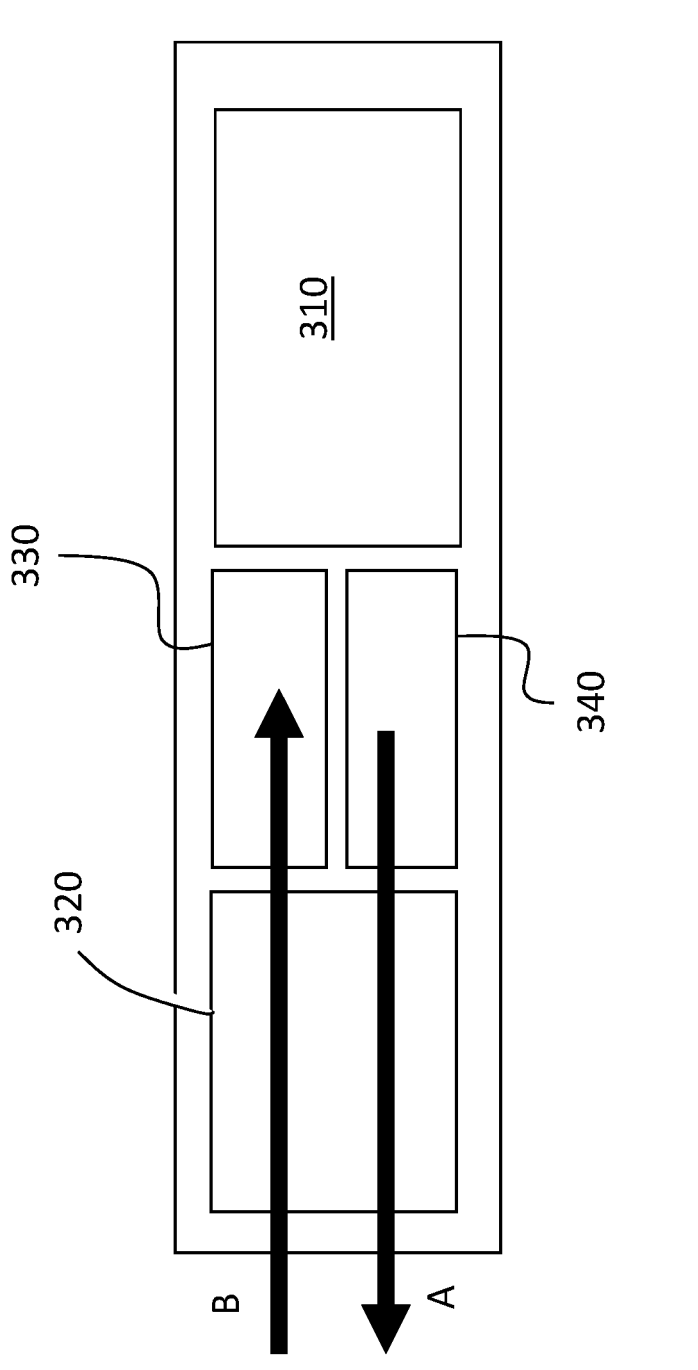

Referring now to FIG. 3, there is shown a schematic diagram of non-combustible aerosol delivery system 300. The system 300 has a power source 310, a mouthpiece 320, and a filter unit 330. The system 300 also has a unit containing vapor forming material 340. The unit 340 may be heated or the like to produce an aerosol. During inhalation, the unit 340 may provide an aerosol for inhalation. The aerosol flows along inhalation airflow pathway A towards the mouthpiece 320 and to the user. The user may then exhale into the system 300, if the filter unit 330 is engaged, and the vapor may be processed by the filter unit 330 in the system 300. Use of the unit 340 prevents the user having to handle the vapor forming material directly. Exhaling into the system 300 may be more hygienic for people in the vicinity of the user.

The system 300 may have vapor forming material (or aerosol generating material) in a unit 340. The unit 340 containing the vapor forming material may be arranged within the system 300 disclosed herein as separate to the power source 310 and the filter unit 330. In an example, the power source 310 may be arranged at a distal end of the system 300. The unit 340 containing the vapor forming material may be proximal to and connected to the power source 310, as the unit 340 may use power so as to form vapor from the vapor forming material, such as use of electrical power to generate a vapor from heating a vapor forming material. The filter unit 330 may be at a proximal end of the system 330 (not in the example of FIG. 3) such that the vapor from the unit 340 containing the vapor forming material may pass the vapor to the mouthpiece 320 or outlet near the user for inhalation prior to the user exhaling back into the system 300. Such an arrangement may be specifically advantageous for arrangements of air-flow and electrical connections.

Figure 4:
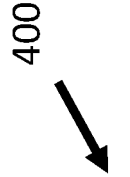
FIG. 4 schematically shows a longitudinal cross-sectional view of an example of a non-combustible aerosol delivery system.
Figure 4:
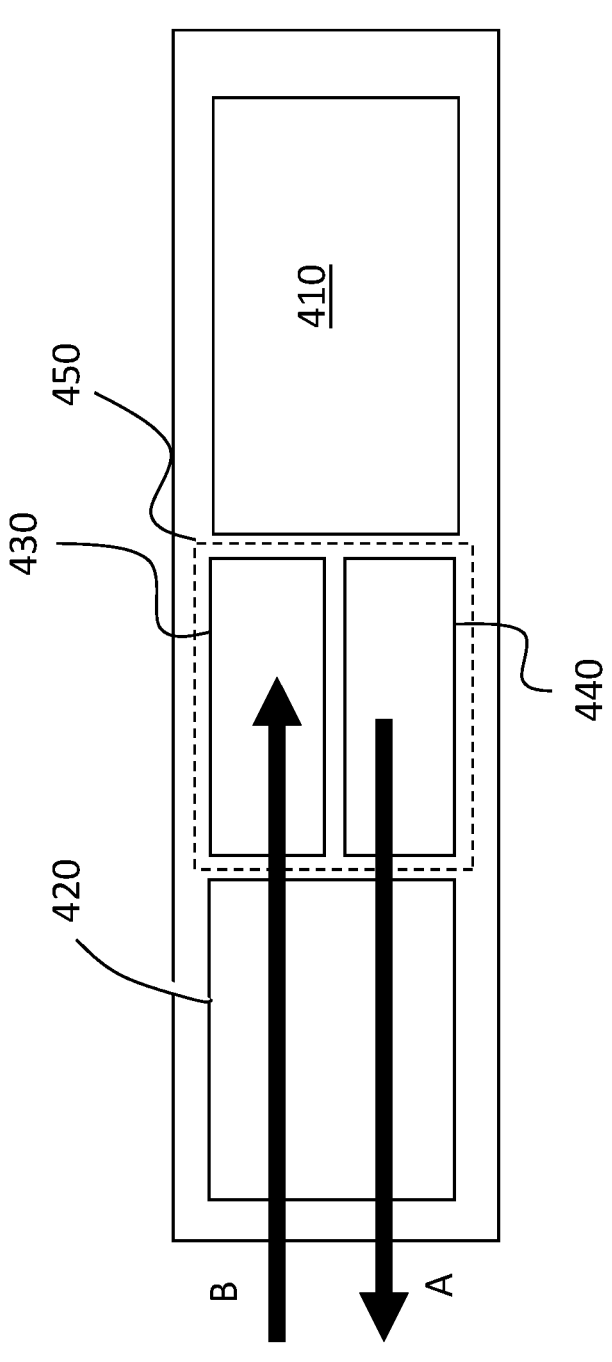

Referring now to FIG. 4, there is shown a schematic diagram of non-combustible aerosol delivery system 400. The system 400 has a power source 410, a mouthpiece 420, a filter unit 430 and a unit containing vapor forming material 440. In the example shown, the filter unit 430 and the unit containing the vapor forming material 440 are formed together as a single assembly 450 which is removable from the non-combustible aerosol delivery system 400.

The manufacturer can tailor the lifetime of the unit containing the vapor forming material 440 and the filter in the filter unit 430 to end at a similar time such that the user can remove and replace the single assembly 450 at a suitable time for both elements.

Relatedly, this may enable easy removable of one portion of the system 400 (the single assembly 450) which may need more regular cleaning than e.g. the section of the system 400 containing the power source 410. As airflow need not pass through the power source 410, there is less likelihood of regular cleaning being needed at the power source 410. By enabling cleaning of a portion which requires cleaning more regularly, the overall lifetime of the system 400 is increased.

In examples wherein the single assembly 450 is not designed to be thrown away, replacement filters or the like may be inserted into the single assembly 450 as the filter unit 430 ages with use. Again, this will increase the overall lifetime of the system 400 and prevent the full system 400 being thrown away after a filter unit 430 is depleted. The vapor forming material unit 440 may also be removed from the single assembly 450 and replaced to increase the lifetime of the system 400.

Alternatively, the single assembly 450 may be used and discarded, after use, for replacement with another single assembly 450. This arrangement would prevent a user needing to contact vapor forming material which can be unpleasant and difficult to handle. In this way, the user's experience of the system 400 is improved. Furthermore, discarding only the single assembly 450 ensures the power source 410 portion of the system 400 is not wastefully thrown away. The power source 410 may, in any example herein, be rechargeable and therefore not in need of being discarded but rather recharged.

The vapor forming material may comprise a plant material. The vapor forming material may be a liquid.

Figure 5:
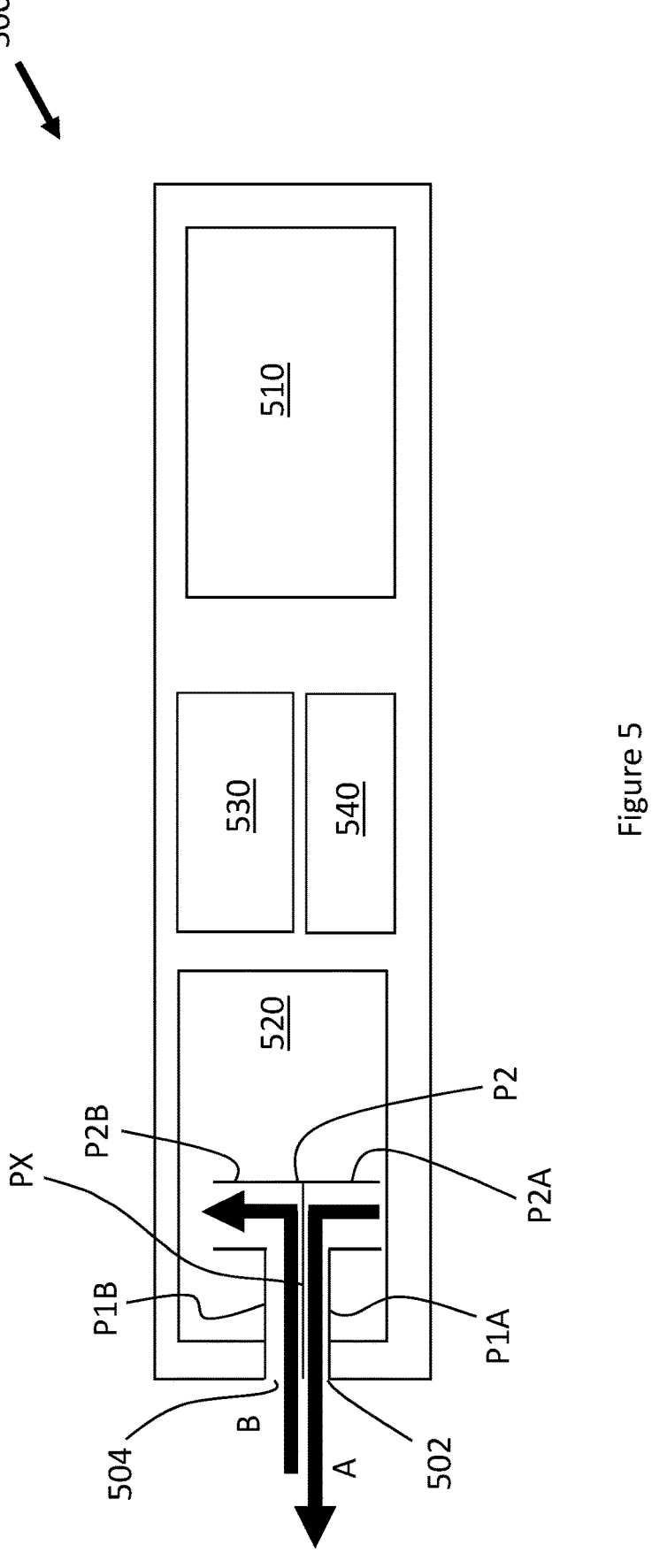
FIG. 5 schematically shows a longitudinal cross-sectional view of an example of a non-combustible aerosol delivery system.

Referring now to FIG. 5, there is shown a schematic diagram of a non-combustible aerosol delivery system 500. The non-combustible aerosol delivery system 500 of FIG. 5 has a power source 510, a mouthpiece 520, a filter unit 530 and a vapor forming material unit 540. The non-combustible aerosol delivery system 500 has inhalate airflow path A and exhalate airflow path B. The non-combustible aerosol delivery system 500 has an outlet 502 through which inhalate airflow path A may pass and an inlet 504 through which exhalate airflow path B may pass.

The arrangement of FIG. 5 is similar to that of FIG. 4, however passages along which the inhalate and exhalate travel are shown in more detail. The passage of the inhalate is shown, at least partially, in passage portion P1A and P2A. The passage of the exhalate is shown, at least partially, in passage portion P1B and P2B. Between these passage portions P1A, P1B, P2A, P2B is arranged a separating portion PX.

Though not shown, the inhalation airflow path A may begin at vapor generating medium unit 540 or the like and travel along passage portion P2A into the mouthpiece 520 to reach passage portion P1A. Inhalation airflow path A then travels along inhalation airflow passage portion P1A through the mouthpiece 520 to the outlet 502 and to the user.

Exhalation airflow path B enters exhalation airflow passage portion P1B at the inlet 504. The exhalation airflow path B passes along exhalation airflow passage portion P1B and then along passage portion P2B. Though not shown in FIG. 5, the passage portion P2B may carry the exhalate through the mouthpiece 520 to the filter unit 530 for processing (as in FIG. 4).

In this example, therefore, the inhalate airflow path A and the exhalate airflow path B are entirely distinct from each other. In this way, the system 500 prevents any exhalate being re-inhaled on a subsequent puff. Each inhalation is along a passage path that the previous exhalation cannot take. Therefore, each inhalation cannot be tainted by accidental inclusion of material left over (via condensation or otherwise) from the previous exhalation into the system 500. This provides a more repeatable and familiar vapor for inhalation and prevents unintended changes in the vapor composition. In turn, this improves the user's experience of the system. The outlets 502, 504 may be contained in separate mouthpieces such that a user inhales on one mouthpiece and exhales into another.

Figure 6:
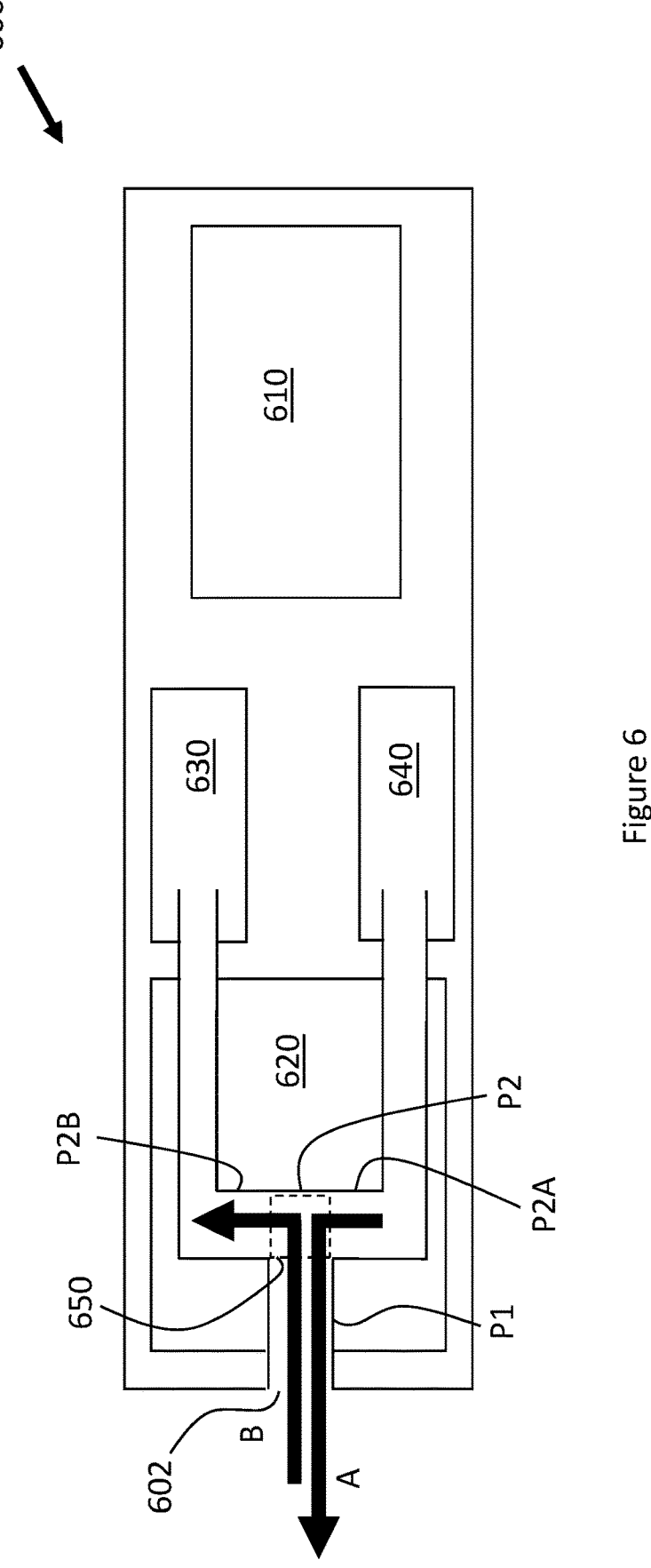
FIG. 6 schematically shows a longitudinal cross-sectional view of an example of a non-combustible aerosol delivery system.

Referring now to FIG. 6, there is shown a schematic diagram of a non-combustible aerosol delivery system 600. The non-combustible aerosol delivery system 600 of FIG. 6 has a power source 610, a mouthpiece 620 and a filter unit 630. The non-combustible aerosol delivery system 600 has inhalate airflow path A and exhalate airflow path B. The non-combustible aerosol delivery system 600 has an outlet 602 through which inhalate airflow path A and exhalate airflow path B pass.

In the example of FIG. 6, a portion P1 of the inhalate airflow path A and a portion P1 of the exhalate airflow path B are the same. Utilizing the same path for a portion P1 of the inhalate and exhalate airflow paths A, B allows the option of using one outlet 602 in the system 600. In this way, the number of components in the system 600 is reduced which, in turn, may increase the overall lifetime of the system 600. Similarly, a shared portion P1 allows for more compact conformations of the system 600, which can lead to an improved user experience with the system 600. E.g. the system 600 of FIG. 6 needs not have two mouthpieces or outlets, rather needing only one mouthpiece 620 with one outlet 602.

The inhalate airflow path A and exhalate airflow path B are shown. Both paths A, B enter a pathway P1 which branches at P2. Inhalate airflow path A enters pathway P1 from branch P2A. Exhalate airflow path B exits pathway P1 into branch P2B. In this way, the two airflow paths A, B share portion P1 of the pathway P1, P2.

Inhalate airflow path A is shown as coming from an aerosol generating component 640 to the outlet 602 of the mouthpiece 620. Exhalate airflow path B is shown as going to a filter unit 630 from the outlet 602 of the mouthpiece 620. The aerosol generating component 640 may include a heater and aerosolizable material arrangement so that, in use, a vapor is produced for inhalation.

The system 600 has a mouthpiece portion 650 which is configured to move between an inhalation position and an exhalation position, wherein in the inhalation position the mouthpiece 620 is in fluid communication with the remainder of the inhalate airflow path and is not in fluid communication with the remainder of the exhalate airflow path, and wherein in the exhalation position the mouthpiece 620 is not in fluid communication with the remainder of the inhalate airflow path and is in fluid communication with the remainder of the exhalate airflow path. The portion 650 may effectively block one path while opening the other and vice versa.

In an example, the mouthpiece portion 650 is a diverter assembly 650. The diverter 650 is shown in dotted lines. Such a diverter assembly 650 may be arranged to allow, during inhalation, passage of the inhalate airflow from passage portion P2A to passage portion P1 and prevent, during inhalation, any airflow from passage portion P1 to passage portion P2B. The diverter assembly 650 may be arranged to allow, during exhalation, passage of the exhalate airflow from passage portion P1 to passage portion P2B during exhalation and prevent, during exhalation, any airflow from passage portion P2A to passage portion P1. In this way, the system 600 provides for a controlled passage of exhalate airflow to the filter for processing while avoiding the exhalate interacting with, and depleting, the aerosol generating material in aerosol generating component 640. The diverter assembly 650 may be a multi-flap valve, wherein the flaps of the multi-flap valve have a thickness of no greater than 0.7 mm such as no greater than 0.5 mm.

Figures 7A, 7B:
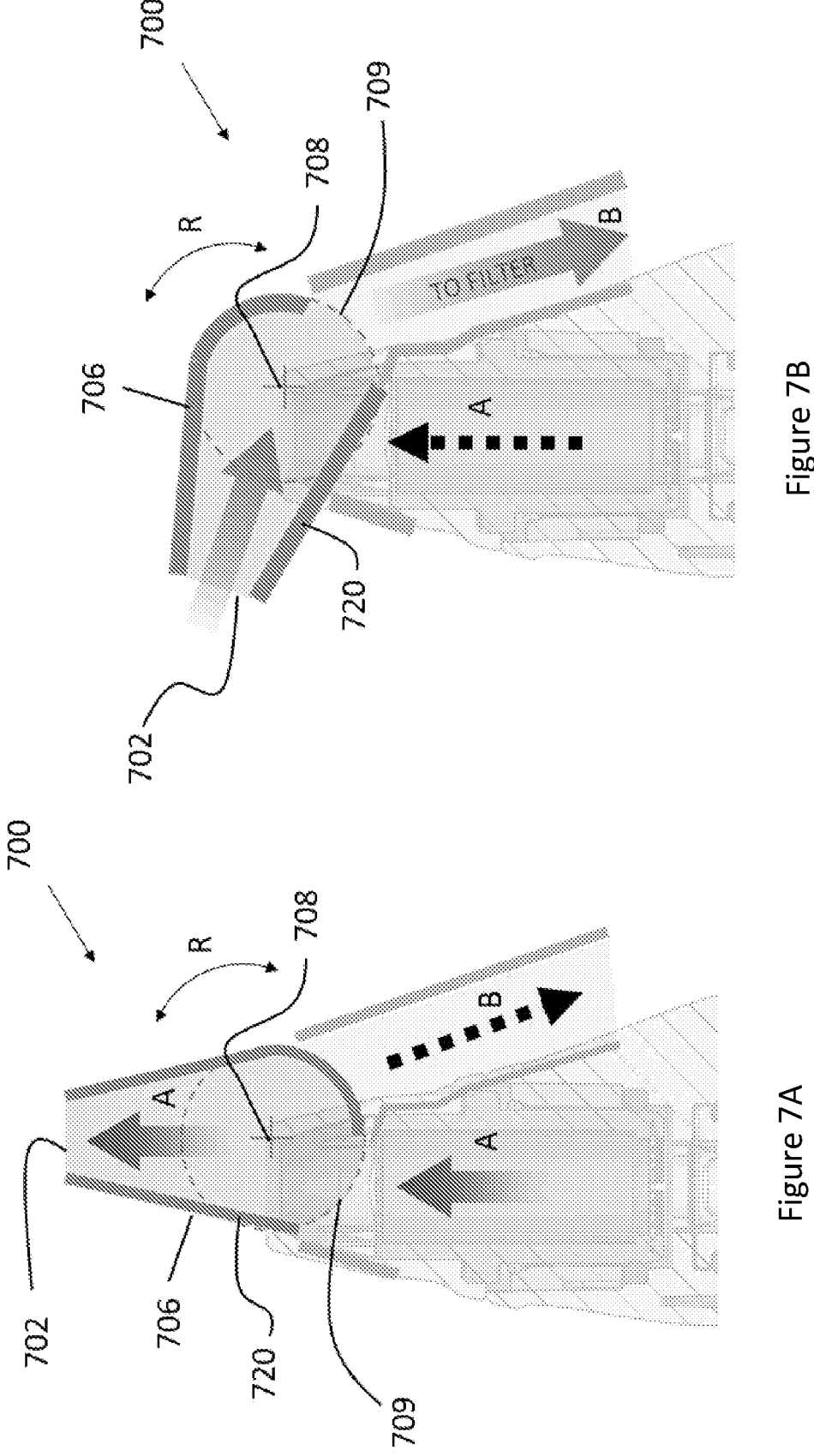
FIGS. 7A and 7B schematically show sectional views of examples of non-combustible aerosol delivery systems.

Referring now to FIGS. 7A and 7B, there are shown sectional views of a non-combustible aerosol delivery system 700. Although not shown, the non-combustible aerosol delivery system 700 has similar features to the previous examples of FIGS. 1A to 6.

The non-combustible aerosol delivery system 700 of FIG. 7A has inhalate airflow path A and exhalate airflow path B. The non-combustible aerosol delivery system 700 has an outlet 702 through which inhalate airflow path A and exhalate airflow path B may pass. The system 700 also has a movable portion 706 as part of the mouthpiece 720. The system 700 has a hinge 708. The mouthpiece 720 is hinged by hinge 708 so as to rotate in the direction shown by arrow R between the inhalation position (FIG. 7A) and the exhalation position (FIG. 7B). The system 700 of FIGS. 7A and 7B have an inlet port/outlet port 709 which, in the inhalation position (FIG. 7A), is in fluid communication with the remainder of the inhalate airflow path A and is not in fluid communication with the remainder of the exhalate airflow path B and vice versa for the exhalation position (FIG. 7B).

The inhalation position is shown in FIG. 7A. The inhalation airflow path A leads from inside the system 700 to the outlet 702 in FIG. 7A. The exhalation airflow path B is shown as prevented in FIG. 7A and is therefore in dashed lines.

The exhalation position is shown in FIG. 7B. The exhalation airflow path B leads from the outlet 702 to the filter of system 700 in FIG. 7B. The inhalation airflow path A is shown as prevented in FIG. 7A and is therefore in dashed lines.

Use of rotation allows for the system 700 to be designed ergonomically, as it utilizes a portion of the mouthpiece 720 for both pathways A, B. In this way, the system 700 may be made more compact and therefore be easier to handle and store for a user.

The mouthpiece in the systems described may therefore move to allow airflow to pass between different passages within the system. The movement of the mouthpiece may block one passage and open another. In one embodiment, a spring loaded mouthpiece is arranged to move between an inhalation position and an exhalation position. Other mechanical or electrical elements such as a slider may be used to move the mouthpiece so as to engage one pathway or the other. The mechanical elements such as the slider, or the like, may move the mouthpiece or the valve. Electric valves may be used (e.g. flexible solenoid valves) which may be activated by a button or the like on the system.

Any combination of valves, passages, divertors, spring-loaded or bias mechanisms may be used in the system. Thicknesses of valves have been considered and values of thicknesses 0.1 mm to 0.7 mm such as 0.1 mm to 0.5 mm have been found to be particularly effective. These have been found to balance the requirements of valve activation tensile strength and pressure drop. In particular, 0.1 mm flap thicknesses have been found to provide an advantageous pressure drop such that user experience is not impaired during exhalation. The thinner the flap, the less pressure required to move it. Such flaps have in examples demonstrated minor leakage issues and therefore thicker flaps may be advantageous in certain instances. In particular, 0.5 mm flap thickness have shown greater liquid retention and therefore do not exhibit leakage as readily. As such, 0.5 mm or thicker valves (say 0.7 mm) may be selected as the valve thickness when liquid loss is particularly undesirable. 0.3 mm thickness is a middle point enabling both good pressure drop and good prevention of leakage.

In examples, an acceptable pressure drop is around 300 Pa for a reasonable user experience of the system. As such, a valve thickness may be selected to not affect the pressure drop more than around 300 Pa. Of course, the valve and the filter may both contribute to pressure drop, though not necessarily in a linear manner, and the overall effect can be calculated to be around 300 Pa while providing effective filtering. The examples shown herein provide such an advantageous balance.

Figure 8:
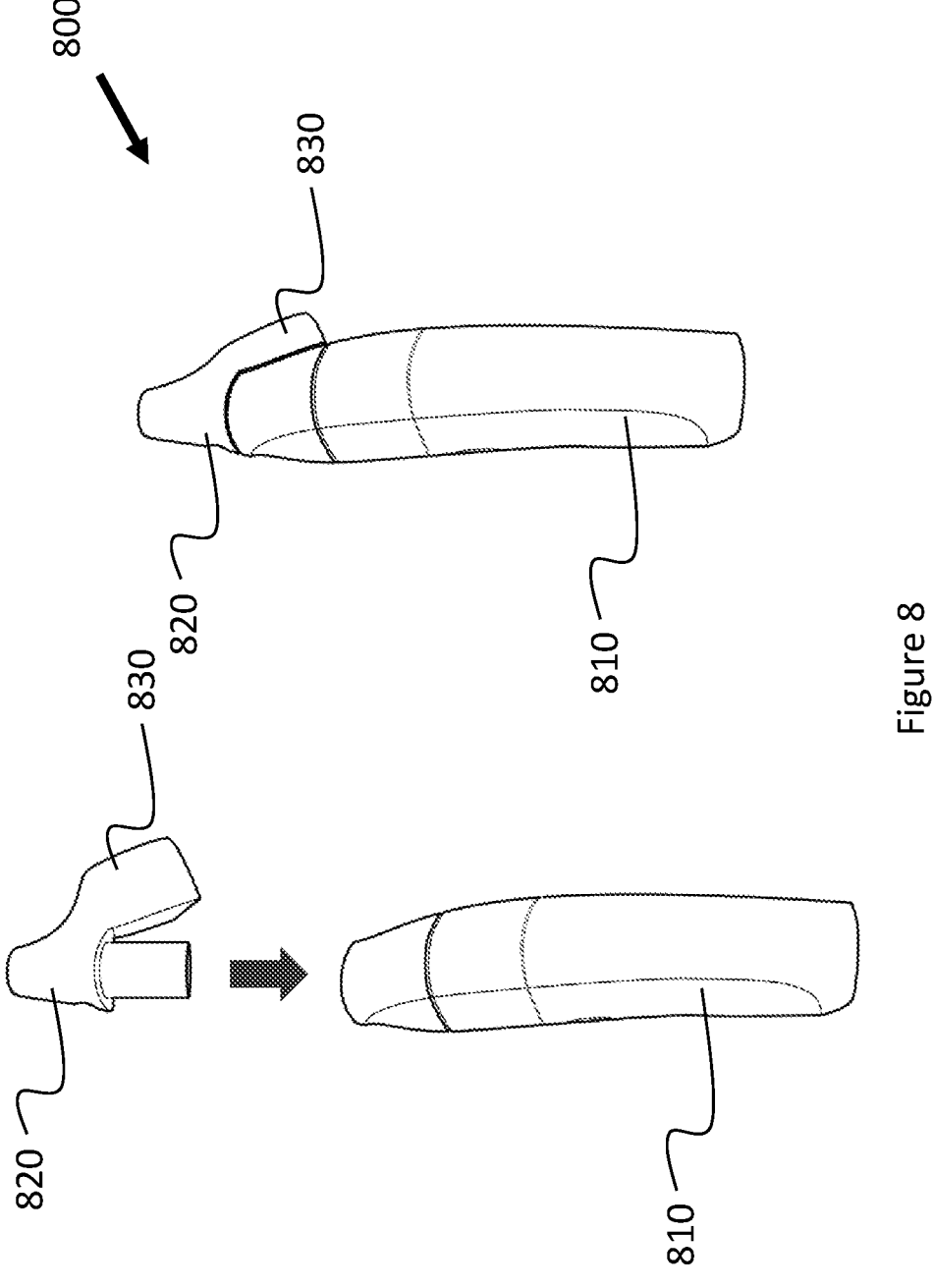
FIG. 8 schematically shows views of an example of a non-combustible aerosol delivery system.

Referring now to FIG. 8, there is shown a schematic diagram of a non-combustible aerosol delivery system 800. The non-combustible aerosol delivery system 800 of FIG. 8 has a power source 810, a mouthpiece 820 and a filter unit 830.

The filter unit 830 is formed as part of the mouthpiece 820 in the example of FIG. 8. The size of the filter unit 830 is dependent on the required filter area which may depend on the choice of filter in the filter unit 830 and the effectiveness of that filter unit 830. Therefore, it may be advantageous for the filter 830 to be arranged away from the main body of the system 800 so as to impact least on the main shape and size of the system 800. Airflow may be directed into the filter unit 830 by any of the methods described above.

Figure 9:
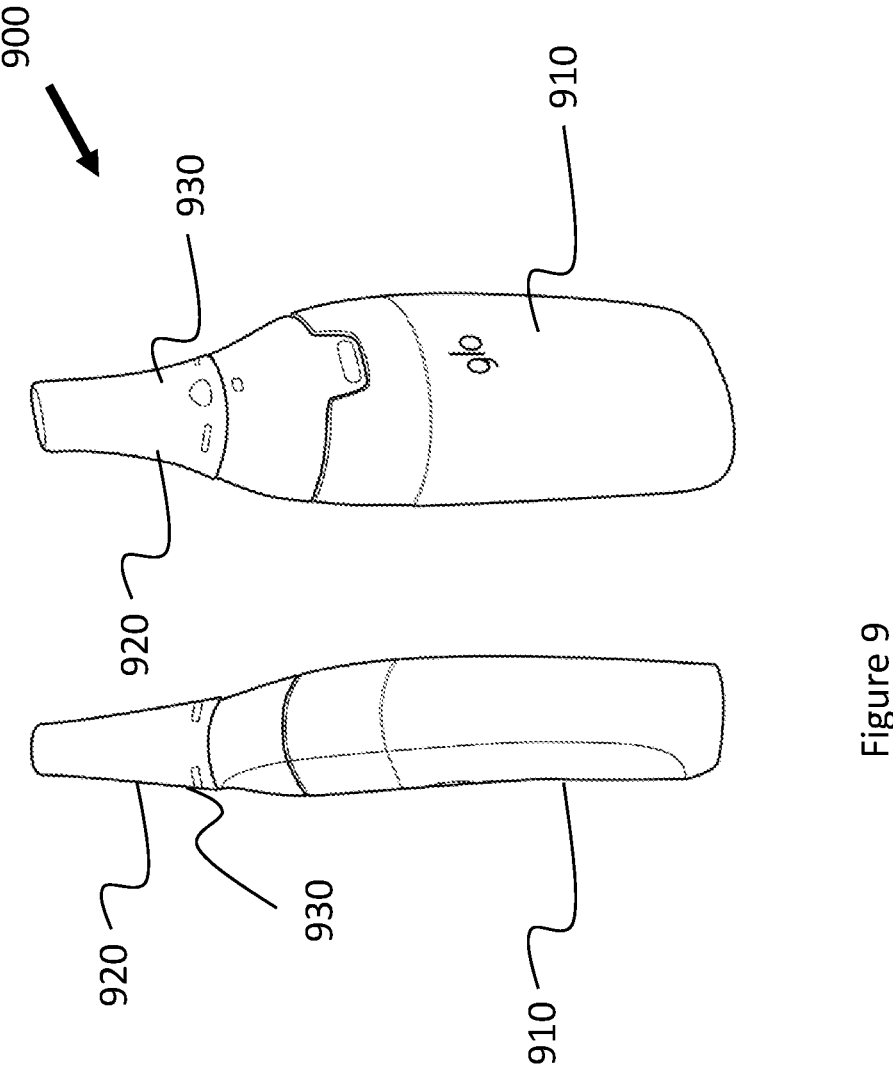
FIG. 9 schematically shows views of an example of a non-combustible aerosol delivery system.

Referring now to FIG. 9, there is shown a schematic diagram of a non-combustible aerosol delivery system 900. The non-combustible aerosol delivery system 900 of FIG. 9 has a power source 910, a mouthpiece 920 and a filter unit 930.

The filter unit 930 is formed as part of the mouthpiece 920 in the example of FIG. 9. The size of the mouthpiece/filter unit 920, 930 is dependent on the required filter area which may depend on the choice of filter in the filter unit 930 and the effectiveness of that filter unit 930. Therefore, it may advantageous for the filter 930 to be arranged away from the main body of the system 900 so as to impact least on the main shape and size of the system 900.

In the example of FIG. 9, the mouthpiece/filter unit 920,930 is elongated when compared to the arrangement shown in FIG. 2, where the filter unit 230 is separate, and when compared to the arrangement shown in FIG. 8, where the filter unit 830 is a bulk addition to one side of the mouthpiece 820. Airflow may be directed into the filter unit 930 by any of the methods described above. The impact on size of the filter unit in each of these depends on the efficacy of the filter. Selection of an effective filter is therefore advantageous in producing a compact system.

The filter unit may therefore contain at least one filter comprising a material selected from glass fiber, polypropylene, and combinations thereof. These filters have been found to be particularly effective in removing droplets from vapor.

The filter unit may be arranged to effectively collect vapor from the breath of a user. This may be by use of a filter in the filter unit comprising a material selected from glass fiber. In other examples, the filter unit may have additionally or alternatively a filter which is a high-efficiency particulate air (HEPA) filter. The HEPA filter may be formed from non-woven glass filament sheets of fabric, cellulosic 'paper' sheets or plastic fibers. These may be formed into a high surface area filter through corrugation and the use of a tortuous path. HEPA filters may be made of either micro glass fibers, or polymers, or a mixture of both (a combination can be used to make filters stronger when pleating). Polymers are seen to have a small benefit in electrostatic attraction of particles. In other examples, the filter unit may have additionally or alternatively a filter which comprises a material selected from polypropylene.

Other filter materials that may be used include borosilicate glass (glass microfiber Whatman particle retention in liquid 2.7 μm), isopore hydrophilic polycarbonate (pore size 0.2 μm), hydrophilic nylon mesh (pore size 10-11 μm), lint free cloth and polypropylene (pore size 0.4 μm).

Each of these filters have shown to be particularly advantageous at retaining vapor.

The system therefore is able to remove vapor from the breath of a user which is exhaled through exhalate flow path B. Furthermore, the system is able to remove vapor from the exhalate by, for example, use of a separator for separating aerosol droplets from vapor. In a specific example, the filter unit comprises a vortex separator for removing aerosol droplet from vapor. This advantageously combines with the materials for the filter in the filter unit to more efficiently remove vapor from the exhalate flow.

In an example, the system can further comprise a complex flow path separator. The complex flow separator may be part of the filter unit or separate from the filter unit. The complex flow path separator may divert or redirect exhalate flow in the system. In an example, the complex flow path separator elongates the path along which the exhalate flow travels which enables more separation of the aerosol droplets from the vapor. In turn, this enables a more efficient system for receiving and processing an exhalate flow. Reducing pressure drop across the system during the exhalation of a user is advantageous as the user experience a lesser flow restriction. In this way, as the above elements perform the function of the system while reducing the pressure drop, the user experience is improved.

In an example, the filter unit further comprises a water filtration unit. The water filtration unit may comprise water through which exhalate may be passed to filter it. Water filtration works by passing bubbles of vapor through a liquid to impact them, in this case water. This technique is particularly effective as vapor bubbles has a large water-vapor surface area for interaction, but other liquids may be used. This technique may be used alongside others to collect vapor from the exhalate breath of a user.

In an example, the filter unit may comprise at least one deodorizing filter. Advantageously, the deodorizing filter allows for removal of undesirable odor from exhaled vapor. This can therefore improve the user's experience of the system. The at least one deodorizing filter may comprise at least one filter comprising activated carbon. Activated carbon is a particularly effective deodorizing filter.

In an example, the filter unit may comprise at least one filter comprising activated carbon. Activated carbon allows absorption of volatile compounds which may be present in the exhalate. Removing and absorbing these is of particular advantage to prevent the volatile compounds impacting other components of the system. A further advantage relates to the pressure drop experienced with activated carbon, which is similar to types of aerosolizable material that may be used with the present system to generate an aerosol for inhalation by a user. Therefore, the user may experience little or no pressure drop during the exhalation breath. Therefore, in turn, this further improves the user's experience of the system. Activated carbon may be provided in a block or the like which a number of bores through the block for allowing the passage of exhalate.

The non-combustible aerosol delivery device may have a generally cylindrical shape, extending along a longitudinal axis, and may comprise two main components, optionally a control body (containing the power source) and a cartomizer (containing the filter unit). The cartomizer may include an internal chamber containing a reservoir of a payload such as for example a liquid comprising nicotine, a vaporizer (such as a heater), and a mouthpiece. References to 'nicotine' herein will be understood to be merely exemplary and can be substituted with any suitable active ingredient. References to 'liquid' as a payload herein will be understood to be merely exemplary and can be substituted with any suitable payload such as botanical matter (for example tobacco that is to be heated rather than burned), or a gel comprising an active ingredient and/or flavoring. The reservoir may comprise a foam matrix or any other structure for retaining the liquid until such time that it is required to be delivered to the vaporizer. In the case of a liquid/flowing payload, the aerosol generating component is for vaporizing the liquid, and the cartomizer may further include a wick or similar facility to transport a small amount of liquid from the reservoir to a vaporizing location on or adjacent the aerosol generating component. In the present disclosure, a heater is used as a specific example of an aerosol generating component. However, it will be appreciated that other forms of aerosol generating component (for example, those which utilize ultrasonic waves) could also be used and it will also be appreciated that the type of aerosol generating component used may also depend on the type of payload to be vaporized.

The power source may include a re-chargeable cell or battery to provide power to the non-combustible aerosol delivery system. The power source may also include a circuit board for generally controlling the non-combustible aerosol delivery system. In an example, when the aerosol generating component receives power from the battery, which may be controlled by the circuit board, the aerosol generating component vaporizes the liquid and this vapor is then inhaled by a user through a mouthpiece. In some specific embodiments the body is further provided with a manual activation device, e.g. a button, switch, or touch sensor located on the outside of the body.

The control body and cartomizer may be detachable from one another, but are joined together when the system is in use by a connection to provide mechanical and electrical connectivity between the control body and the cartomizer. The electrical connector on the control body 20 that is used to connect to the cartomizer may also serve as a socket for connecting a charging device (not shown) when the control body is detached from the cartomizer. The other end of the charging device may be plugged into a USB socket to re-charge the cell in the control body of the non-combustible aerosol delivery device which may be an e-cigarette. In other implementations, a cable may be provided for direct connection between the electrical connector on the control body and a USB socket.

The non-combustible aerosol delivery device is provided with one or more holes for air inlets. These holes connect to an air passage through the electronic aerosol provision device to the mouthpiece. When a user inhales through the mouthpiece, air is drawn into this air passage through the one or more air inlet holes, which are suitably located on the outside of the non-combustible aerosol delivery device. When the heater is activated to vaporize the nicotine from the cartridge, the airflow passes through, and combines with, the generated vapor, and this combination of airflow and generated vapor then passes out of the mouthpiece to be inhaled by a user. Except in single-use devices, the cartomizer may be detached from the control body and disposed of when the supply of liquid is exhausted (and replaced with another cartomizer if so desired).

In some cases, the non-combustible aerosol delivery device may comprise means to control aspects of the airflow in the system. A portion of the airflow pathway providing a fluid communication path between the mouthpiece and one or more air inlet holes in the device to may be provided with features which are movable to change the shape of the airflow pathway (e.g. the topology of the walls bounding the air flow path), and thereby change characteristics of airflow in the non-combustible aerosol delivery device. For instance, movable features (such as valves, baffles or inlets) may enable modification of operating parameters such as the resistance to draw of the system, the degree of turbulence in the airflow pathway, the direction of airflow in the vicinity of aerosol generating component, and the condensation path distance between the aerosol generating component and the mouthpiece.

In some examples, the resistance to draw of the device can be modified by providing means to selectively open or close one or more air inlets configured to allow air into the air passage comprised in the device. In some examples, elements may be provided to change the direction of airflow into or out of the system. In this way, the flow paths of inhalate airflow path A and exhalate airflow path B may be controlled. For example, a slider may be provided on the outer housing of the system, configured to be moved to different positions (e.g. rotated about an axis or displaced along an axis). The slider may be mechanically or electrically connected so as to cause a resulting change in the pathways A, B such as via movement of a baffle or valve or the like.

In some examples, the slider may be actuated by an electromechanical actuator such as a linear or rotational actuator, and the actuator position controlled by the control circuitry to adjust the position of components controlling the form of airflow paths A,B. Other features may be included in the device to modify the airflow through the device, controlled by the control circuitry in a similar manner. For example, one or more moveable baffles, or a mechanical aperture, or one or more air inlets may be disposed in an air passage of the system near the aerosol generating component or, e.g., the mouthpiece. These features may be moved into different positions to adjust the manner in which incident airflow exits the aerosol generating component or enters/exits the mouthpiece of the system.

For example, one or more baffles may be moved to direct airflow into portion P1 of the pathway through the system 200 (during inhalation) and into portion P2B of the pathway through the system 200 (during exhalation).

It will be appreciated that the non-combustible aerosol delivery devices shown in FIGS. 1 to 3 are presented by way of example, and various other implementations can be adopted. For example, in some embodiments, the cartomizer may be provided as two separable components, namely a cartridge comprising the liquid reservoir and mouthpiece (which can be replaced when the liquid from the reservoir is exhausted), and an aerosol generating component comprising a heater (which is generally retained). As another example, the charging facility may connect to an additional or alternative power source, such as a car cigarette lighter.

As used herein, non-combustible aerosol provision systems, or non-combustible aerosol delivery systems, are systems that release compounds from an aerosol-generating material without combusting the aerosol-generating material, such as electronic cigarettes, tobacco heating products, and hybrid systems to generate aerosol using a combination of aerosol-generating materials.

According to the present disclosure, a "non-combustible" aerosol provision system is one where a constituent aerosol-generating material of the aerosol provision system (or component thereof) is not combusted or burned in order to facilitate delivery of at least one substance to a user.

In Some Embodiments, the Delivery System is a Non-Combustible Aerosol Provision System, Such as a Powered Non-Combustible Aerosol Provision System.

In some embodiments, the non-combustible aerosol provision system is an electronic cigarette, also known as a vaping device or electronic nicotine delivery system (END), although it is noted that the presence of nicotine in the aerosol-generating material is not a requirement.

In some embodiments, the non-combustible aerosol provision system is an aerosol-generating material heating system, also known as a heat-not-burn system. An example of such a system is a tobacco heating system.

In some embodiments, the non-combustible aerosol provision system is a hybrid system to generate aerosol using a combination of aerosol-generating materials, one or a plurality of which may be heated. Each of the aerosol-generating materials may be, for example, in the form of a solid, liquid or gel and may or may not contain nicotine. In some embodiments, the hybrid system comprises a liquid or gel aerosol-generating material and a solid aerosol-generating material. The solid aerosol-generating material may comprise, for example, tobacco or a non-tobacco product.

Typically, the non-combustible aerosol provision system may comprise a non-combustible aerosol provision device and a consumable for use with the non-combustible aerosol provision device.

In some embodiments, the disclosure relates to consumables comprising aerosol-generating material and configured to be used with non-combustible aerosol provision devices. These consumables are sometimes referred to as articles throughout the disclosure.

In some embodiments, the non-combustible aerosol provision system, such as a non-combustible aerosol provision device thereof, may comprise a power source and a controller. The power source may, for example, be an electric power source or an exothermic power source. In some embodiments, the exothermic power source comprises a carbon substrate which may be energized so as to distribute power in the form of heat to an aerosol-generating material or to a heat transfer material in proximity to the exothermic power source.

In some embodiments, the non-combustible aerosol provision system may comprise an area for receiving the consumable, an aerosol generator, an aerosol generation area, a housing, a mouthpiece, a filter and/or an aerosol-modifying agent.

In some embodiments, the consumable for use with the non-combustible aerosol provision device may comprise aerosol-generating material, an aerosol-generating material storage area, an aerosol-generating material transfer component, an aerosol generator, an aerosol generation area, a housing, a wrapper, a filter, a mouthpiece, and/or an aerosol-modifying agent.

The foregoing discussion discloses and describes merely exemplary embodiments of the present disclosure. As will be understood by those skilled in the art, the present disclosure may be embodied in other specific forms without departing from the essential characteristics thereof. Accordingly, the content of the present disclosure is intended to be illustrative, but not limiting of the scope of the disclosure, as well as of the claims. The disclosure, including any readily discernible variants of the teachings herein, defines, in part, the scope of the foregoing claim terminology.

The invention claimed is:

1. A non-combustible aerosol delivery system for filtering exhaled breath, the non-combustible aerosol delivery system comprising:
   a power source;
   a mouthpiece; and
   a removable filter unit, wherein:
      in a first configuration, the removable filter unit is present and is in engagement with the non-combustible aerosol delivery system to provide:
      an inhalate airflow path adapted to convey vapor generated by
      the non-combustible aerosol delivery system to a user during an inhalation, and
      an exhalate airflow path adapted to convey breath from the user during an exhalation into the non-combustible aerosol delivery system to the removable filter unit, and
      in a second configuration, the removable filter unit is not in engagement with the non-combustible aerosol delivery system, wherein the mouthpiece comprises a diverter assembly, wherein the diverter assembly comprises a multi-flap valve, and wherein the flaps of the multi-flap valve have a thickness of no greater than 0.7 mm.

2. The non-combustible aerosol delivery system of claim 1, wherein in the first configuration the removable filter unit is disposed between the mouthpiece and the power source of the non-combustible aerosol delivery system.

3. The non-combustible aerosol delivery system of claim 1, further comprising a unit containing a vapor-forming material.

4. The non-combustible aerosol delivery system of claim 3, wherein the vapor-forming material comprises a plant material.

5. The non-combustible aerosol delivery system of claim 3, wherein the vapor-forming material is a liquid.

6. The non-combustible aerosol delivery system of claim 1, wherein the inhalate airflow path and the exhalate airflow path are entirely distinct from each other.

7. The non-combustible aerosol delivery system of claim 1, wherein the mouthpiece forms both a portion of the inhalate airflow path and a portion of the exhalate airflow path, and is configured to move between an inhalation position and an exhalation position, wherein in the inhalation position the mouthpiece is in fluid communication with a remainder of the inhalate airflow path and is not in fluid communication with a remainder of the exhalate airflow path, and wherein in the exhalation position the mouthpiece is not in fluid communication with the remainder of the inhalate airflow path and is in fluid communication with the remainder of the exhalate airflow path.

8. The non-combustible aerosol delivery system of claim 7, wherein:
   the mouthpiece is hinged so as to rotate between the inhalation position and the exhalation position, or
   the mouthpiece is rotatable to move between the inhalation position and the exhalation position.

9. The non-combustible aerosol delivery system of claim 7, wherein the mouthpiece has an inlet port which, in the inhalation position, is in fluid communication with the remainder of the inhalate airflow path and is not in fluid communication with the remainder of the exhalate airflow path, and an outlet port which, in the exhalation position, is not in fluid communication with the remainder of the inhalate airflow path and is in fluid communication with the remainder of the exhalate airflow path.

10. The non-combustible aerosol delivery system of claim 9, wherein:
   the inlet port and the outlet port are the same, or
   the inlet port and the outlet port are distinct from each other.

11. The non-combustible aerosol delivery system of claim 1, wherein the removable filter unit contains at least one filter comprising glass fiber, polypropylene, or combinations of glass fiber and polypropylene thereof.

12. The non-combustible aerosol delivery system of claim 1, wherein the removable filter unit further comprises a separator for separating aerosol droplets from vapor.

13. The non-combustible aerosol delivery system of claim 1, wherein the removable filter unit comprises at least one deodorizing filter.

14. The non-combustible aerosol delivery system of claim 1, wherein the non-combustible aerosol provision system is an electronic cigarette.

15. The non-combustible aerosol delivery system of claim 1, wherein the non-combustible aerosol provision system is an aerosol generating material heating system.

16. The non-combustible aerosol delivery system of claim 1, wherein the non-combustible aerosol provision system generates aerosol using a combination of aerosol-generating materials, and wherein at least one of the aerosol-generating materials is heated.

17. A mouthpiece for use in a non-combustible aerosol delivery system for filtering exhaled breath, wherein, in use, in a first configuration, the mouthpiece is in fluid communication with a filter of the non-combustible aerosol delivery system to provide:
   an inhalate airflow path adapted to convey vapor generated by the non-combustible aerosol delivery system through the mouthpiece to a user during an inhalation, and an exhalate airflow path adapted to convey breath from the user during an exhalation through the mouthpiece to the filter unit;

wherein, in use, in a second configuration, the mouthpiece is not in fluid communication with the filter of the non-combustible aerosol delivery system, wherein the mouthpiece comprises a diverter assembly, wherein the diverter assembly comprises a multi-flap valve, and wherein the flaps of the multi-flap valve have a thickness of no greater than 0.7 mm.

* * * * *